(12) United States Patent
Bernegger-Egli et al.

(10) Patent No.: US 6,780,634 B1
(45) Date of Patent: Aug. 24, 2004

(54) METHOD FOR PRODUCING (1R,4S)-2-AZABICYCLO[2.2.1]-HEPT-5-EN-3-ON DERIVATIVES

(75) Inventors: Christine Bernegger-Egli, Münster (CH); Frank Brux, Raron (CH); Jean Paul Roduit, Grône (CH); Oleg Werbitzky, Visp (CH); Yves Guggisberg, Sierre (CH)

(73) Assignee: Lonza AG, Gampel-Wallis (CH)

( * ) Notice: Subject to any disclaimer, the term of this patent is extended or adjusted under 35 U.S.C. 154(b) by 0 days.

(21) Appl. No.: 09/743,391
(22) PCT Filed: Jul. 8, 1999
(86) PCT No.: PCT/EP99/04814
§ 371 (c)(1),
(2), (4) Date: Apr. 17, 2001
(87) PCT Pub. No.: WO00/03032
PCT Pub. Date: Jan. 20, 2000

(30) Foreign Application Priority Data

Jul. 9, 1998 (EP) .............................................. 98112719
Dec. 17, 1998 (EP) .............................................. 98123949

(51) Int. Cl.[7] ................................................ C12P 13/00
(52) U.S. Cl. ....................... 435/280; 435/128; 435/122; 435/136; 435/147; 435/227
(58) Field of Search ................................ 435/280, 128, 435/122, 136, 147, 227

(56) References Cited

U.S. PATENT DOCUMENTS 5,688,933 A   11/1997   Evans et al. ................ 536/22.1

FOREIGN PATENT DOCUMENTS

| WO | 9810075 | 3/1998 |
| WO | 9910519 | 3/1999 |
| WO | WO 99/10519 | * 3/1999 |

OTHER PUBLICATIONS

Nakano et al., Tetrahedron: Asymmetry (1996), 7(8), 2382–2386.*
Campbell et al., "Chirospecific Syntheses of Precursors of Cyclopentane and Cyclopentene Carbocyclic Nucleosides by [3+3]–Coupling and Transannular Alkylation", J. Org. Chem. 1995, 60:4602–4616.
Katagiri et al., "A Highly Efficient Synthesis of the Antiviral Agent (+)–Cyclaradine Involving the Regioselective Cleavage of Epoxide by Neighboring Participation", Tetrahedron Letters 1997 38:1961.
Taylor et al. "Development of the Biocatalytic Resolution of 2–azabicyclo[2.2.1]hept–5–en–3–one as an entr to Single–Enantiomer Carbocyclic Nucleosides", 1993 Tet. Asymmetry 4:1117.

Csuk et al., "Biocatalytical Transformations, IV. Enantioselective Enzymatic Hydrolyses of Building Blocks for the Synthesis of Carbocyclic Nucleosides", Tetrahedon: Asymmetry, 1994 5:269–76.
Evans et al., "Potential Use of Carbocyclic Nucleosides for the Treatment of AIDS: Chemo–enzymatic Syntheses of the Enantiomers of Carbovir", J. Chem. Soc. Perkin Trans. Jan. 1992, 5:589–592.
Brabban, J., "Stereospecific (–lactamase activity in a *Pseudomonas fluorescens*species", Industrial Microboil. 1996 16:8–14.

* cited by examiner

Primary Examiner—Irene Marx
(74) Attorney, Agent, or Firm—Baker Botts L.L.P.

(57) ABSTRACT

A biotechnological method is described for preparing compounds of the general formulas

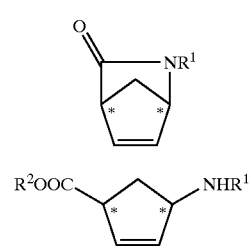

wherein $R^1$ is acyl or acyloxy and $R^2$ is a hydrogen atom or $C_{1-10}$ alkyl, comprising the conversion of a lactam of the general formula

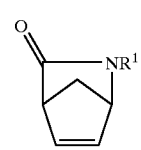

by means of a hydrolase in the presence of a nucleophile and in the presence of a base in a constant pH range.

Also described is the subsequent conversion of the compound of general formula I into the optically active 1-amino-4-(hydroxymethyl)-2-cyclopentene of the formula

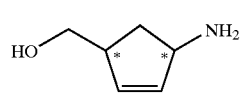

22 Claims, No Drawings

METHOD FOR PRODUCING (1R,4S)-2-AZABICYCLO[2.2.1]-HEPT-5-EN-3-ON DERIVATIVES

CROSS-REFERENCE TO RELATED APPLICATIONS

This application is a national phase application of International Application No. PCT/EP99/04814, which was filed on Jul. 8, 1999 and which published on Jan. 20, 2000, which in turn claims priority from European Application No. 98112719.4, which was filed on Jul. 9, 1998, and European Application No, 98123949.4, which was filed on Dec. 17, 1998.

DESCRIPTION

The invention's method for preparing compounds of the general formulas

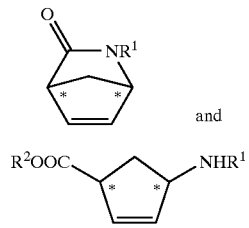

and wherein $R^1$ is acyl, alkoxycarbonyl or aryloxycarbonyl and $R^2$ is a hydrogen atom or $C_{1-10}$ alkyl, comprises treating with a hydrolase and an effective amount of a nucleophile and a base in a constant pH range a racemic lactam of the formula

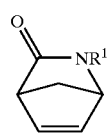

Formula I compounds, such as, for example, (1R,4S)-2-acetyl-2-azabicyclo[2.2.1]hept-5-ene-3-one are important intermediates for preparing (1R,4S)-1-amino4hydroxymethyl)-2-cyclopentene, which, in turn, is an important intermediate for preparing carbocyclic nucleosides, such as, for example, Carbovir (Campbell et al. J. Org. Chem. 1995, 60, 4602–4616). Formula II compounds, such as, for example, the propyl ester of (1S,4R)-acetylamino-2-cyclopentene-1-carboxylic acid, are an important intermediate for preparing (1S,4R)-1-amino-4-(hydroxymethyl)-2-cyclopentene, which similarly can be an important intermediate for preparing carbocyclic nucleosides.

Only the chemical preparation of (1R,4S)-2-acetyl-2-azabicyclo[2.2.1]hept-5-ene-3-one by acylating (1R,4S)-2-azabicyclo[2.2.1]hept-5-ene-3-one (Katagiri et al., Tetrahedron Letters, 1997, 38, 1961) is known. According to this method, (1R,4S)-2-acetyl-2-azabicyclo[2.2.1]hept-5-ene-3-one can be obtained only from the corresponding (1R,4S)-2-azabicyclo[2.2.1]hept-5-ene-3-one as an educt. This educt is too expensive.

The problem involved in this invention was to develop a method for preparing compounds of general formula I and II, which can be prepared from easily obtainable, inexpensive starting material with good enantiomer purity.

This problem is solved with the new biotechnological method according to claim 1.

The invention's method for preparing compounds of the general formulas

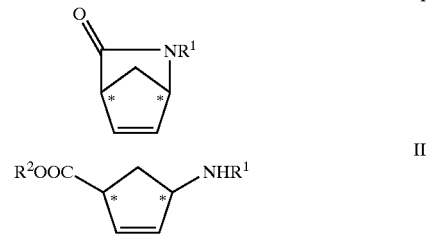

wherein $R^1$ is acyl or acyloxy and $R^2$ is a hydrogen atom or $C_{1-10}$ alkyl, takes place by means of a hydrolase in the presence of a nucleophile and in the presence of a base in a constant pH range starting with a racemic lactam of the formula

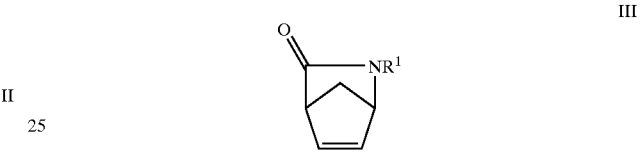

The starting material, the lactam of the general formula III (substrate), can be prepared, for example, according to Taylor et al. (Tet. Asymmetry; 4, 1993,1117).

$C_{1-10}$ alkyl is linear or branched and substituted or unsubstituted. Examples of $C_{1-10}$ alkyl are methyl, ethyl, propyl, butyl, isobutyl, t-butyl, isopropyl, pentyl, hexyl, heptyl, octyl, nonyl or decyl and its isomers, as well as chloromethyl, bromomethyl, dichloromethyl, dibromomethyl, chloropropyl and bromobutyl.

Acyl means alkanoyl or arylcarbonyl. Alkanoyl is suitably $C_{1-4}$ alkanoyl, which can be substituted or unsubstituted. Substituted $C_{1-4}$ alkanoyl in the following is understood to be substituted with one or more halogen atoms. Examples of $C_{1-4}$ alkanoyl are acetyl, propionyl, butyryl, chloroacetyl, bromoacetyl and dichloroacetyl. Arylcarbonyl is suitably benzylcarbonyl or phenylcarbonyl, substituted or unsubstituted.

Acyloxy means alkoxycarbonyl or aryloxycarbonyl. Alkoxycarbonyl is suitably $C_{1-4}$ alkoxycarbonyl, such as methoxycarbonyl, ethoxycarbonyl, propoxycarbonyl, butoxycarbonyl or t-butoxycarbonyl (BOC). Aryloxycarbonyl is suitably benzyloxycarbonyl or phenyloxycarbonyl.

$R^1$ is preferably $C_{1-4}$ alkanoyl or $C_{1-4}$ alkoxycarbonyl, in particular acetyl or ethoxycarbonyl.

Hydrolases that can be used are proteases or lipases, preferably proteases, such as serine proteases. Examples of serine proteases that can be used are chymotrypsin, trypsins and subtilisins (bacterial serine proteases). Subtilisins that can be used are commercial subtilisins, such as subtilisin A, subtilisin B, alcalases, ALK enzyme bacillopeptidase A, bacillopeptidase B, bioprases, colistinases, esperases, genenase I, kazusase, maxacal, maxatases, nagarses, peptidases, protease S, protease VIII, protease XXVII, proteinases, such as the alkaline proteinase of Bacillus subtilis or Aspergillus oryzae, proteinase K from Tritirachium album, savinases, subtilopeptidasen, superases, and thermoases. Conducting the biotransformation by means of savinases is preferred. Suitable savinases are savinase 12 Type W™, savinase 16.0 L Type EX™, savinase 32.0 L Type EX™, savinase 4.0 T Type W™, and savinase 8.0 L™. The lipase that can be used is, for example, lipase from Candida Antarctica.

If the hydrolases used are proteases, such as proteases from *Bacillus subtilis*, proteases from *Aspergillus oryzae*, proteinase K from Tritirachium album, the (1S, 4R) enantiomer in the racemic lactam of formula III is hydrolyzed suitably into the corresponding compound of general formula II, whereby the (1R, 4S) enantiomer of general formula I is obtained. If the hydrolases used are lipases, such as lipase from Candida Antarctica, the (1R, 4S) enantiomer in the racemic lactam of formula III is hydrolyzed suitably into the corresponding compound of general formula II, whereby the (1S, 4R) enantiomer of general formula I is obtained.

Water or $C_{1-10}$ alcohols can be used as the nucleophile. Suitable $C_{1-10}$ alcohols are methanol, ethanol, propanol, isopropanol, butanol, t-butanol, isobutanol, pentanol, hexanol, heptanol, octanol, nonanol or decanol. If the nucleophile used is a $C_{1-10}$ alcohol, the corresponding ester of general formula II ($R^2=C_{1-10}$ alkyl) is formed, as the expert knows. If water is used as the nucleophile, obviously, the corresponding acid of general formula II ($R^2=H$) is formed.

Depending on the hydrolase and the substrate (formula III lactam), the biotransformation is conducted suitably between pH 5 and 12, preferably between pH 6 and 8. In the invention, for a given hydrolase and a given substrate, the pH value is maintained constant in the presence of a base. The pH value is suitably maintained constant at +/−0.5 pH units by addition of a base. If, for example, the substrate is racemic 2-acetyl-2-azabicyclo[2.2.1]hept-5-ene-3-one ($R^1$=acetyl) and savinase is used as the hydrolase, the pH value is held constant at preferably between pH 7.0 and pH 7.5.

An inorganic or organic base can be used as the base. For example, KOH and NaOH are suitable as inorganic bases. A suitable organic base can be, for example, triethanolamine dissolved in an organic solvent. If one of the aforesaid alcohols is used as the nucleophile, the corresponding alcoholate can serve as the base.

The biotransformation is suitably conducted in water, a buffer solution, a $C_{1-10}$ alcohol or in a mixture of these with an aprotic organic solvent. Suitable aprotic organic solvents are, for example, ether and aromatic hydrocarbons. Tetrahydrofuran, dioxane or t-butyl methyl ether can be used as the ether. Toluene and benzene are suitable aromatic hydrocarbons. The buffer solutions used can be, for example, low molarity, such as 10–100 mM sodium or potassium phosphate buffer, hepes buffer. The $C_{1-10}$ alcohols used can be those previously described.

The biotransformation can also be conducted so that the lactam of general formula III serves as solvent. Then the biotransformation is suitably conducted in the presence of half of the stoichiometric quantities of water or the corresponding alcohol.

Depending on the solvent, the biotransformation can be conducted in a two-phase or one-phase system. The biotransformation is advisedly conducted in a one-phase system.

After a usual conversion time of a few hours depending on the selected starting material, the desired optically active compounds of general formulas I and II are obtained in outstanding yields and enantiomer purity. The preferred starting materials are racemic 2-acetyl-2-azabicyclo-[2.2.1]hept-5-ene-3-one ($R^1$=acetyl) and the racemic 2-ethoxycarbonyl-2-azabicyclo-[2.2.1]hept-5-ene-3-one ($R^1$=ethoxycarbonyl). The preferred compounds of formula II are (1S, 4R)-4-acetylamino-2-cyclopentene-1-carboxylic acid ($R^1$=acetyl, $R^2$=H), (1S, 4R)-4-ethoxycarbonylamino-2-cyclopentene-1-carboxylic acid ($R^1$=ethoxycarbonyl, $R^2$=H), (1S, 4R)-4-acetylamino-2-cyclopentene-1-carboxylic acid methyl ester ($R^1$=acetyl, $R^2$=$CH_3$), (1S, 4R)-4-acetylamino-2-cyclopentene-1-carboxylic acid butyl ester ($R^1$=acetyl, $R^2$=$C_4H_9$), (1S. 4R)-4-acetylamino-2-cyclopentene-1-carboxylic acid ethyl ester ($R^1$=acetyl, $R^2$=$C_2H_5$), and (1S, 4R)-4-acetylamino-2-cyclopentene-1-carboxylic acid propyl ester ($R^1$=acetyl, $R^2$=$C_3H$—). The (1S, 4R)-4-acetylamino-2-cyclopentene-1-carboxylic acid $C_{2-10}$ alkyl esters, preferably the (1S, 4R)-4-acetylamino-2-cyclopentene-1-carboxylic acid ethyl ester and the (1S, 4R)-4-acetylamino-2-cyclopentene-1-carboxylic acid propyl ester of the formula II are not described in the literature and are similarly part of the invention.

Another part of the invention is the subsequent reaction, the reduction of compounds of general formula I to an optically active 1-amino-4-(hydroxymethyl)-2-cyclopentene derivative, in particular to a (1R,4S)-1-amino-4-(hydroxymethyl)-2-cyclopentene derivative of the general formula

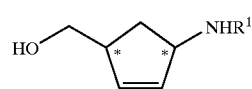

IV wherein $R^1$ is as already named.

The reduction is suitably conducted with binary or complex metal hydrides of the boron or aluminum group, such as alkali metal borohydrides, alkaline earth metal borohydrides, alkali metal aluminum hydrides, alkaline earth metal aluminum hydrides.

The binary alkali metal borohydrides or alkaline earth metal borohydrides used can be $NaBH_4$, $LiBH_4$, $KBH_4$, $NaAlH_4$, $LiAlH_4$, $KAlH_4$, $Mg(BH_4)_2$, $Ca(BH_4)_2$, $Mg(AlH_4)_2$, $Ca(AlH_4)_2$. Complex metal hydrides of the boron or aluminum group can have the general formula $M^1M^2H_4L_m$, wherein n is a whole number from 1 to 4, m is a whole number from 4 to 4-n, $M^1$ is an alkali metal atom, $M^2$ is boron or aluminum, and L is $C_{1-4}$ alkyl, $C_{1-4}$ alkenyl, $C_{1-4}$ alkoxy, CN or an amine, or the complex metal hydrides can have the general formula $M^2H_oL_p$, wherein $M^2$ is as already named, o is a whole number from 0 to 3, and p is a whole number from 3 to 3-o. The $M^1M^2H_nL_m$ used can be $LiBH(C_2H_5)_3$, $LiBH_x(OCH_3)_{4-n}$, wherein x is a whole number from 1 to 3. $LiAlH(OC(CH_3)_3)_3$, $NaAlH_2(OC_2H_4OCH_3)_2$, $NaAlH_2(CH_2H_5)_2$ or $NaBH_3CN$. The reduction is conducted preferably with a metal borohydride, such as sodium borohydride.

The metal hydrides are used suitably in a molar ratio of 0.5 to 1per mole of compound of general formula I.

The reduction is conducted suitably under an inert gas atmosphere, such as, for example, under an argon or nitrogen atmosphere.

The reduction can be conducted at a temperature of −10 to 30° C., preferably 0 to 10° C.

Secondary or tertiary alcohols are suitable as solvents for the reduction. 2-Butanol can be used, for example, as the secondary alcohol, and t-amyl alcohol, for example, as the tertiary alcohol. A secondary alcohol is preferred.

The subsequent conversion, the hydrolysis of the optically active 1-amino-4-(hydroxymethyl)-2-cyclopentene derivatives of formula IV to the corresponding optically active 1-amino4-(hydroxymethyl)-2-cyclopentenes or their salts of the formula

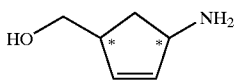

V with an alkaline earth metal hydroxide, alkali metal hydroxide or with a mineral acid is similarly part of the invention. In particular, the (1R,4S)-1-amino-4-(hydroxymethyl)-2-cyclopentene derivative is hydrolyzed to (1R,4S)-1-amino-4-(hydroxymethyl)-2-cyclopentene.

Lithium, sodium or potassium hydroxide is suitable as the alkali metal hydroxide. Barium hydroxide, for example, can be used as the alkaline earth metal hydroxide. The hydrohalide acids such as, for example, hydrochloric acid or hydrobromic acid are suitable as the mineral acids.

The hydrolysis is suitably conducted at a temperature of 50 to 120° C., preferably 90 to 100° C.

Suitable salts of the (1R,4S)-1-amino-4-(hydroxymethyl)-2-cyclopentene (formula V) are its hydrohalide salts, such as hydrochlorides or hydrobromides.

EXAMPLES

Example 1

Preparation of (1R,4S)-1-amino-4-(hydroxymethyl)-2-cyclopentene from racemic (±)-2-acetyl-2-azabicyclo[2.2.1]hept-5-ene-3-one 1.1 Preparation of (1R,4S)-2-acetyl-2-azabicyclo[2.2.1]hept-5-ene-3-one 1.1.1 By savinase in a Mixture of Sodium Phosphate Buffer and Tetrahydrofuran 5 ml tetrahydrofuran were mixed with 3.84 ml 20 mM sodium phosphate buffer pH 7 and 1.16 ml savinase 16.0 L type EX, Novo Nordisk (16 KNPU/g, kilo novo protease units). 417 μl (+/−)-2-acetyl-2-azabicyclo[2.2.1]hept-5-ene-3-one (330 mmoles/l) were added. The reaction was mixed with a magnetic stirrer and maintained at 30° C. by a water bath. The pH value was maintained constant at pH 7 by a pH automatic control system with 1 M NaOH. Samples were taken periodically and analyzed by HPLC for content and enantiomer excess (Chiralpak AD, Daicel Chemical Ltd. (0.46×25 cm) isocratically at room temperature, flow 1 ml/min with n-heptane (ethanol 2%, detection at 215 nm)). A total of 1.25 ml NaOH were used. After 120 minutes, 50% of the quantity of (+/−)-2-acetyl-2-azabicyclo[2.2.1]hept-5-ene-3-one used was hydrolyzed to the corresponding acid. The content was determined with achiral GC. The analysis was conducted with gas chromatography as follows: capillary column: HP-5 (5% phenylmethylsiloxane), temperature gradient 100° C.–260° C.; the samples were diluted in tetrahydrofuran 1:1 for the analysis.

1.1.2 In Water 1.1.2.1 60 ml $H_2O$ and 35 ml savinase were added to 419.25 ml (+/−)-2-acetyl-2-azabicyclo[2.2.1]hept-5-ene-3-one as in example 1.1.1.. The pH value was maintained at 7.5 with 7.5N NaOH. The 1 l Applikon fermenter was stirred at 400 rpm. Samples were taken periodically and analyzed as in Example 1.1.1. An ee [errors excepted] value of 99% was measured after 45 hours.

The charge was filtered by suction through a Whatman GF/F filter, and the filter cake was washed twice with 100 ml and once with 50 ml butyl acetate. The aqueous phase was shaken twice with 200 ml butyl acetate. The organic phase was concentrated in a Rotovap. 144.8 g of product were obtained with an ee value of >98%, which corresponded to a yield of 31% relative to the racemate. The analysis was conducted as in Example 1.1.1.

1.1.2.2 60 ml $H_2O$ and 35 ml savinase were added to 486.3 g (+/−)-2-acetyl-2-azabicyclo[2.2.1]hept-5-ene-3-one (content: 95.4%) as in Example 1.1.1. The pH value was maintained at 7.5 with 7.5N NaOH. The 1 l Applikon fermenter was stirred at 400 rpm. Samples were taken periodically and analyzed as in Example 1.1.1. An ee value of >98% was measured after 45 hours. A total of 174.6 ml 7.5N NaOH were used.

The charge was filtered by suction through a Whatman GF/F filter, and the filter cake was washed twice with 100 ml and once with 50 ml butyl acetate. The aqueous phase was shaken twice with 200 ml butyl acetate. The organic phase was concentrated in a Rotovap. 144.8 g of product were obtained with an ee value of >98% (content: 92.5%), which corresponded to a yield of 29% relative to the racemate. The analysis was conducted as in Example 1.1.1.

1.1.3 In Methanol 72.3 ml (+/−)-2-acetyl-2-azabicyclo[2.2.1]hept-5-ene-3-one (content: 95.4%) were mixed with 8.3 ml savinase as in Example 1.1.1 and 19.4 ml methanol. The reaction mixture was stirred at 30° C. for 24 hours. The pH remained constant at 7.2. Samples were taken as in Example 1.1.1. After 25 hours, an ee value of >98% was reached, and the reaction was ended. The analytical yield was 42% relative to the racemate. The corresponding methyl ester ($R^2=CH_3$) of the compound of general formula II, which was proven by GC-MS, was formed in stoichiometric quantities. The analysis was conducted as in Example 1.1.1.

1.1.4 In Butanol 72.3 ml (+/−)-2-acetyl-2-azabicyclo[2.2.1]hept-5-ene-3-one (content: 95.4%) were mixed with 76.86 ml 1-butanol and 8.3 ml savinase as in Example 1.1.1. The reaction mixture was measured during a time period of 22 hours. After this time, an ee value of >98% was determined with HPLC. The pH value was maintained constant at pH 7.5 with 4 N NaOH. Samples were taken as in Example 1.1.1. The reaction temperature was 30° C. The formation of a free acid ($R^2=H$) of the compound of general formula II was proven with HPLC, and the formation of the butyl ester ($R^1=C_4H_9$) of the compound of general formula II was proven by GC-MS. An analytical yield of 34.8% relative to the racemate was achieved.

1.1.5 By Savinase in 1-Propanol 1.1.5.1 242 g (+/−)-2-acetyl-2-azabicyclo[2.2.1]hept-5-ene-3-one, 168.6 ml 1-propanol and 28 ml savinase as in Example 1.1.1 were incubated at 30° C. and at a pH of 7.0 (adjusted with 4N NaOH). Samples were taken as in Example 1.1.1. After 24 hours, the ee value of the product was determined at % ee=99%. The analytical yield was 47%. 100 ml toluene were added to this mixture (459 ml), and the propanol was evaporated under reduced pressure. The solution was extracted twice with toluene (250 ml) and water (100 ml). The toluene was evaporated and the product distilled. 113.9 g (0.69 mole) of product (purity 93%, ee=99%) corresponding to a yield of 45.7% relative to the racemate were obtained. The analysis was conducted as in Example 1.1.1.

1.1.5.2 208 g (+/−)-2-acetyl-2-azabicyclo[2.2.1]hept-5-ene-3-one (content: 95.4%), 168.6 ml 1-propanol and 23 ml savinase as in Example 1.1.1 were incubated at 30° C. and at a pH of 7.2 (adjusted with 4N NaOH) in an Erlenmeyer flask. After 30 hours, the ee value of the product was determined at % ee=>98%. 100 ml toluene were added to this mixture (459 ml), and the propanol was evaporated under reduced pressure. The solution was extracted twice with toluene (250 ml) and water (100 ml). The toluene was evaporated and the product distilled (12 mbar, 85–95° C.).

79.13 g (0.69 mole) of product (purity 93%, ee >98%) corresponding to a yield of 37% relative to the racemate were obtained. The analysis was conducted as in Example 1.1.1.

1.1.5.3 2.77 kg (+/−)-2-acetyl-2-azabicyclo[2.2.1]hept-5-ene-3-one (content: 95.8%), 1.35 l of 1-propanol and 355.5 ml savinase as in Example 1.1.1 were reacted at 40° C. and at a pH of 7.4 (set by the addition of 92 g 4N NaOH) in a 5 l stirred reactor. The pH value was maintained constant at pH=7.4 by the addition of 4 N NaOH. After 14 hours, the reaction mixture was cooled to room temperature, and the pH of the solution was adjusted to pH=7.0 by the addition of 20% sulfuric acid. After the addition of 1.15 l toluene, the phases were separated, and the organic phase was vacuum-distilled (product fraction at T=72–76° C., p=1 mbar). 1.07 kg of product (content 91%, ee=98.4%) were obtained, corresponding to a yield of 36.5%. The product content was determined by GC in an Optima 5 column (Macherey-Nagel, Germany). The ee of the product was determined by GC on a chiral LipodexE column (Macherey-Nagel, Germany).

1.1.5.4 Isolation of (1S,4R)-acetylamino-2-cyclopentene-1-carboxylic Acid Propyl Ester 345 g of the still residue from Example 1.1.5.3 were mixed with 250 ml ethyl acetate and 1 l hexane, and the mixture was heated to reflux. Two phases formed. The upper phase was separated and cooled slowly to 0° C. The precipitate was filtered off and vacuum-dried at 40° C. 85.6 g of a colorless product were obtained.

The ee value was determined by GC on a chiral Hydrodex-beta-PM column (Macherey-Nagel, Germany), ee=93%.

α[illegible] $_c$(c=1. MeOH)=79.3°

$^1$H-NMR(CDCl$_3$) 5.91 (br, 1 H) 5.89 (s, 2H) 5.07 (m, 1H) 4.07 (t, 2H) 3.50 (m, 1H) 2.46 (m, 1H) 1.96 (s, 3H) 1.90 (m, 1H) 1.67 (m, 2H) 0.96 (t, 3H)

1.1.6 By Protease from *Bacillus Subtilis* in Phosphate Buffer 1.1.6.1 25 mg *Bacillus subtillis* protease (Fluka 82490), 0.45 ml phosphate buffer (100 mM, pH 7.5), 0.5 ml n-propanol and 0.05 ml (+/−)-2-acetyl-2-azabicyclo[2.2.1]hept-5-ene-3were incubated at 30° C. (+/−2° C.). The pH value was maintained at 7.5 by the manual addition of 1 N NaOH, whereby fluctuations of +/−0.5 pH were attained. Samples were taken as in Example 1.1.1. After 6 hours, all of the (+/−)-2-acetyl-2-azabicyclo[2.2.1]hept-5-ene-3-one was converted. 1.5 hours after incubation, the enantiomer excess for (−)-2-acetyl-2-azabicyclo[2.2.1]-hept-5-ene-3-one was >98%. The unisolated yield was 12% relative to the racemate. Content and enantiomer excess were determined as in Example 1.1.1.

1.1.6.2 125 mg *Bacillus subtillis* protease (Fluka 82490), 2.25 ml phosphate buffer (100 mM, pH 7.5), 2.5 ml n-propanol and 0.25 ml (+/−)-2-acetyl-2-azabicyclo[2.2.1]hept-5-ene-3-one (content: 95.4%) were incubated at 30° C. (+/−2° C.). The pH value was maintained at 7.5 by the manual addition of 1 N NaOH, whereby fluctuations of +/−0.5 pH were attained. Samples were taken as in Example 1.1.1. After 6 hours, 90% of the (+/−)-2-acetyl-2-azabicyclo[2.2.1]hept-5-ene-3-one was converted. 1.5 hours after incubation, the enantiomer excess for (−)-2-acetyl-2-azabicyclo[2.2.1]hept-5-ene-3-one was >98%. The unisolated yield was 12% relative to the racemate.

1.1.7 By Protease from Aspergillus Oryzae in Phosphate Buffer 1.1.7.1 25 mg Aspergillus oryzae (Sigma P-4032, 3.5 units/mg), 0.45 ml phosphate buffer (100 mM, pH 7.5), 0.5 ml n-propanol and 0.05 ml (+/−)-2-acetyl-2-azabicyclo[2.2.1]hept-5-ene-3-one were incubated at 30° C. (+/−2° C.). The pH value was maintained at 7.5 by the manual addition of 1 N NaOH, whereby fluctuations of +/−0.5 pH were attained. Samples were taken as in Example 1.1.1. After 0.5 hour, all of the (+)-2-acetyl-2-azabicyclo[2.2.1]hept-5-ene-3-one converted. The enantiomer excess for (−) 2-acetyl-2-azabicyclo[2.2.1]hept-5-ene-3-one was >98%. The analytical yield relative to (−) 2-acetyl-2-azabicyclo[2.2.1]hept-5-ene-3-one was >40% relative to the racemate. Content and enantiomer excess were determined as in Example 1.1.1.

1.1.7.2 125 mg Aspergillus oryzae (Sigma P-4032, 3.5 units/mg), 2.25 ml phosphate buffer (100 mM, pH 7.5), 2.5 ml n-propanol and 0.25 ml (+/−) 2-acetyl-2-azabicyclo[2.2.1]hept 5-ene-3-one (content: 95.4%) were incubated at 30° C. (+/−2° C.). The pH value was maintained at 7.5 by the manual addition of 1 N NaOH,.whereby fluctuations of +/−0.5 pH were attained. Samples were taken as in Example 1.1.1. After 0.5 hour, all of the (+) 2-acetyl-2-azabicyclo[2.2.1]hept-5-ene-3-one was converted. The enantiomer excess for (−) 2-acetyl-2-azabicyclo-[2.2.1]hept-5-ene-3-one was >98%. The analytical yield relative to (−) 2-acetyl-2-azabicyclo-[2.2.1]hept-5-ene-3-one was >40% relative to the racemate.

1.1.8 By Proteinase K from Tritirachium Albumin in Phosphate Buffer 1.1.8.1 25 mg proteinase K (Sigma P-8044, 1–7 units/mg), 0.45 ml phosphate buffer (100 mM, pH 7.5), 0.5 ml n-propanol and 0.05 ml (+/−) 2-acetyl-2-azabicyclo[2.2.1]hept-5-ene-3-one were incubated at 30° C. (+/−2° C.). The pH value was maintained at 7.5 by the manual addition of 1 N NaOH, whereby fluctuations of +/−0.5 pH were attained. Samples were taken as in Example 1.1.1. After 0.5 hour, all of the (+) 2-acetyl-2-azabicyclo[2.2.1]hept-5-ene-3-one converted. The enantiomer excess for (−) 2-acetyl-2-azabicyclo[2.2.1]hept-5-ene-3-one was >98%. The analytical yield relative to (−) 2-acetyl-2-azabicyclo[2.2.1]hept-5-ene-3-one was 40% relative to the racemate. Content and enantiomer excess were determined as in Example 1.1.1.

1.1.8.2 125 mg proteinase K (Sigma P-8044, 1–7 units/mg), 2.25 ml phosphate buffer (100 mM, pH 7.5), 2.5 ml n-propanol and 0.25 ml (+/−) 2-acetyl-2-azabicyclo[2.2.1]hept-5-ene-3-one (content: 95.4%) were incubated at 30° C. (+/−2° C.). The pH value was maintained at 7.5 by the manual addition of 1 N NaOH, whereby fluctuations of +/−0.5 pH were attained. Samples were taken as in Example 1.1.1. After 0.5 hour, all of the (+) 2-acetyl-2-azabicyclo[2.2.1]hept-5-ene-3-one was converted. The enantiomer excess for (−) 2-acetyl-2-azabicyclo[2.2.1]hept-5-ene-3-one was >98%. The analytical yield relative to (−) 2-acetyl-2-azabicyclo[2.2.1]-hept-5-ene-3-one was 30% relative to the racemate.

1.2 Preparation of (1S,4R)-2-acetyl-2-azabicyclo[2.2.1]hept-5-ene-3-one (by Lipase from Candida Antarctica)

1.2.1 25 mg SP525 (Novo Nordisk), 0.45 ml phosphate buffer (100 mM, pH 7.5), 0.5 ml n-propanol and 0.05 ml (+/−) 2-acetyl-2-azabicyclo[2.2.1]hept-5-ene-3-one were incubated at 30° C. (+/−2° C.). The pH value was maintained at 7.5 by the manual addition of 1N NaOH, whereby fluctuations of +/−0.5 pH were attained. Samples were taken as in Example 1.1.1. After 0.5 hour, all of the (−) 2-acetyl-2-azabicyclo[2.2.1]hept-5-ene-3-one was converted. The enantiomer excess for (−)(1S,4R)-2-acetyl-2-azabicyclo[2.2.1]hept-5-ene-3-one was >98%. The analytical yield relative to (+) 2-acetyl-2-azabicyclo[2.2.1]hept-5-ene-3-one was 12% racemate. Content and enantiomer excess were determined as described in Example 1.

1.2.2 250 mg SP525 (Novo Nordisk), 2.25 ml phosphate buffer (100 mM, pH 7.5), 2.5 ml n-propanol and 2.25 ml (+/−) 2-acetyl-2-azabicyclo[2.2.1]hept-5-ene-3-one (content were incubated at 30° C. (+/−2° C.). The PH value was maintained at 7.5 by the manual addition of 1 N NaOH, whereby fluctuations of +/−0.5 pH were attained. Samples were taken as in Example 1.1.1. After 16 hours, all of the (+/−)-2-acetyl-2-azabicyclo[2.2.1]hept-5-ene-3-one converted. The enantiomer excess for (+)(1S,4R)-2-acetyl-2-azabicyclo[2.2.1]-hept-5-ene-3-one was >98%. The analytical yield relative to (+) 2-acetyl-2-azabicyclo[2.2.1]hept-5-ene-3-one was 12% relative to the racemate.

1.3 Reduction of (1R,4S)-2-acetyl-2-azabicyclo[2.2.1]hept-5-ene-3-one to (1R,4S)-1-acetylamino-4-(hydroxymethyl)-2-cyclopentene.

1.3.1 8 g $NaBH_4$ were added portionwise to a solution of (1R,4S)-2-acetyl-2-azabicyclo[2.2.1]hept-5-ene-3-one (50 g, 0.33 mole), 40 ml water and 240 ml 2-butanol, and the temperature was maintained below 5° C. After 1 hour, the reaction was stopped, and the reaction mixture was adjusted to pH 2.0 with concentrated HCl. The reaction temperature was maintained below 10° C. The pH value was adjusted to pH 9.0 with 30% NaOH. Sodium metaborate was filtered off and the aqueous phase was extracted three times with 2-butanol. After evaporation of the 2-butanol, 49.3 g of product (0.28 mole) were obtained, corresponding to a yield of 88%.

1.3.2 287.4 g (−)-acetyl-2-azabicyclo[2.2.1]hept-5-ene-3-one (100%==>−255 ml, 97%; 1.9 moles) were dissolved in 380 ml water and 1217 ml 2-butanol. The solution was cooled to 0 to 2° C. 45 g $NaBH_4$ (1.188 moles, 1.25 eq.) were suspended in 304 ml fresh 2 butanol in another stirring device. The $NaBH_4$ suspension as added to the solution during 1–2 hours. The reaction was exothermic, and the temperature was not allowed to exceed 5° C. The temperature had to be at 0° C. before a portion was added. The reaction was followed by DC (thin-layer chromatography) (hexane/etrol/MeOH: 551). The reaction was allowed to continue for 1 to 2 hours after the addition. When the reaction as complete (educt concentration had to be at <1.0%), the pH was adjusted to 2 with ca. 135 g concentrated hydrochloric acid. The temperature as maintained below 10° C. The pH was then adjusted immediately to 9 with ca. 85 ml 30% sodium hydroxide solution. The precipitated salts were filtered and washed with 127 ml fresh 2-butanol. The filtrate and the "2-butanol wash" were combined, and the phases separated. The aqueous phase as extracted twice with 380 ml fresh 2-butanol each time. The 2-butanol phases were combined. Ca. 2450 g of a 10% solution of the product (1R,4S)-1-acetylamino-4-(hydroxymethyl)-2-cyclopentene, were obtained in 2-butanol. This corresponded to ca. 250 g of 100% product, (1R,4S)-1-acetylamino-4-(hydroxymethyl)-2-cyclopentene, corresponding to a yield of 85%.

1.4 Hydrolysis of (1R,4S)-1-acetylamino-4-(hydroxymethyl)-2-cyclopentene to (1R,4S)-1-amino-4-(hydroxymethyl)-2-cyclopentene.

1.4.1 30% NaOH (45 g) was added to 49.3 g (0.28 mole) (1R, 4S)-1-acetylamino-4-(hydroxymethyl)-2-cyclopentene, and the suspension was heated to 100° C. After 3.5 hours, the solution was cooled to 0° C. and then adjusted to pH=1.0 with concentrated HCl. Water was evaporated and NaCl filtered off. Pentanol (2 ml per go of residue) and acetone (6 ml per gram of residue) were added. The resulting precipitate was filtered and washed with 20 ml acetone. 37.5 g (0.24 mole) of product were obtained as the hydrochloride salt having an ee=99%, corresponding to a yield of 86%.

1.4.2 85.4 g (1R,4S)-(−)-1-acetylamino-4-(hydroxymethyl)-2-cyclopentene 100% (0.55 mole) was prepared as a 10% solution in 2-butanol. It was distilled until the distillate ceased. Then 100.0 g of a 30% sodium hydroxide solution (==>33.0 g NaOH 100%; 0.825 mole, 1.5 eq) and 65 g water were added. The remaining 2-butanol was removed (with ca.1 10 g water) by azeotropic distillation. The solution was heated at reflux (100–100° C.) for 4–5 hours. The reaction was followed by GC. When the conversion was complete the reaction was cooled to 50° C., and 154 ml 2-butanol (124.3 g) were added. The phases were separated at 50° C. 915 minutes stirring, phases separate). The aqueous phase (ca. 165 g) was discarded. The organic phasese were combined, and ca. 22 g hydrogen chloride were added at 20–40° C. to make pH 1. Some salts precipitated during the acidification. These salts were filtered off at 20° C., and the filtrate was distilled under standard pressure until 220 ml distillate (ca. 180 g) were collected (boiling temperature ca. 91–92° C.). At ca. 70° C., 176 ml acetone (139.0 g) were added. The suspension was stirred at reflux for 15–30 minutes and then cooled to 5° C. After 1 hour at this temperature was filtered off by suction, and the filter cake was washed with 154 ml acetone. 70 g of (−) of 100% product were obtained, corresponding to a yield of 85%.

Example 2

Preparation of (1R,4S)-2-Ethoxycarbonyl-2-azabicyclo[2.2.1]hept-5-ene-3-one 2.1 Preparation of racemic (±)2-Ethoxycarbonyl-2-azabicyclo [2.2.1]hept-5-ene-3-one 109.13 g racemic 2-azabicyclo[2.2.1]hept-5-ene-3-one were mixed with 182.1 g triethylamine, 6.11 g 4-dimethylaminopyridine and 500 ml acetonitrile. The reaction was heated to 50° C. Then, 195.3 g ethyl chloroformate, dissolved in 150 ml acetonitrile, were added portionwise. The temperature w%as maintained below 55° C. After the reaction ended, the solution was cooled to 20° C. The salts were filtered off and washed with acetonitrile. The filtrate was concentrated at 60° C. and 20 mbar, and then mixed with 1500 ml toluene. Three extractions followed: with 250 ml water, pH 8, with 250 ml acetic acid (1%) and with 250 ml saturated NaCl solution. The organic phase as dried with $MgSO_4$ and concentrated at 80° C. 20 mbar. 167.4 g of a brown oil were obtained. The content by GC was 96% (±)-2-ethoxycarbonyl-2-azabicyclo[2.2.1]hept-5-ene-3-one, which was purified by vacuum distillation, b.p.$_{0.01}$=76.5° C. content (GC): 99.5%, yield: 156.6 g (88.5%).

$^1$H-NMR (CDCl$_3$) 1.33 (t, 3H), 2.19 (d, 1H), 2.38 (d, 1H), 3.43 (s, 1H), 4.26 (m, 2H). 5.04 (s, 1H), 6.68 (m, 1H), 6.92 (m, 1H).

2.2 Preparation of (−)-2-Ethoxycarbonyl-2-azabicyclo [2.2.1]hept-5-ene-3-one

The product was prepared as in Example 2.1, starting from (1R,4S)-(−)-2-azabicyclo[2.2.1]hept-5-ene-3-one.

2.3 Preparation of (1R,4S2-Ethoxycarbonyl-2-azabicyclo [2.2.1]hept-5-ene-3-one

500 µl savinase as in Example 1.1.1, 5 ml n-propanol, 4.5 ml (50 mM phosphate buffer pH 8, /tetrahydrofuran 1/1) and 250 µl (+/−) ethoxycarbonyl-2-azabicyclo[2.2.1]hept-5-ene-3-one were incubated at 40° C. at pH 8. The pH value was maintained at 8 by the manual addition of 1 N NaOH. Samples were taken as in Example 1.1.1. After 4.5 hours, an ee value of >98% was measured for the (−) enantiomer, which was proven by the prepared standard (Example 2.2). The unisolated analytical yield relative to the racemate was 46%.

What is claimed is:

1. A method for forming optically active compounds of the formulae

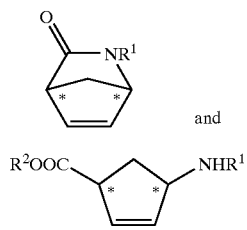

wherein $R^1$ is acyl, alkoxycarbonyl or aryloxycarbonyl and $R^2$ is a $C_{1-10}$ alkyl, the method comprising treating a racemic lactam of the formula

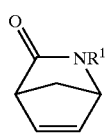

with a hydrolase and an effective amount of a nucleophile, wherein said nucleophile is a $C_{1-10}$ alcohol, and a base in a constant pH range to form the optically active compounds of formulae I and II.

2. The method according to claim 1, wherein a protease or lipase is used as the hydrolase.

3. The method according to claim 2, wherein a serine protease is used as the protease.

4. The method according to claim 3, wherein a subtilisin is used as the serine protease.

5. The method according to claim 1, wherein 2-acetyl-2-azabicyclo[2.2.1]hept-5-ene-3-one or 2-ethoxycarbonyl-2-azabicyclo[2.2.1]hept-5-ene-3-one is used as the racemic lactam of formula III.

6. The method according to claim 1, wherein the treatment of the racemic lactam is conducted in a $C_{1-10}$ alcohol or in a mixture of a $C_{1-10}$ alcohol with an aprotic solvent.

7. The method according to claim 1, wherein the treatment of the racemic lactam is conducted at a temperature of 10 to 60 °C.

8. The method of claim 1, wherein each of the optically active compounds of formulae I and II are isolated after formation.

9. A method for the formation of optically active 1-amino-4-(hydroxymethyl)-2-cyclopentene derivatives of the formula

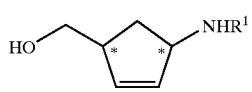

wherein $R^1$ is acyl, alkoxycarbonyl or aryloxycarbonyl, the method comprising treating a racemic lactam of the formula

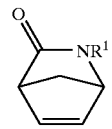

wherein $R^1$ is acyl, alkoxycarbonyl or aryloxycarbonyl with a hydrolase and an effective amount of a nucleophile, wherein said nucleophile is a $C_{1-10}$ alcohol, and a base in a constant pH range to form the compound of the formula

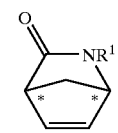

and wherein the compound of formula I is reduced to the compound of formula IV by treatment with a reducing agent.

10. The method of claim 9, wherein each of the optically active 1-amino-4-(hydroxymethyl)-2-cyclopentene derivatives of formula IV are isolated after formation.

11. The method of claim 9, wherein the reducing agent is a metal hydride.

12. A method for the formation of (1R, 4S)-1-amino-4-(hydroxymethyl)-2-cyclopentene of the formula

or its salts, the method comprising treating a racemic lactam of the formula

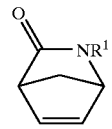

wherein $R^1$ is acyl, alkoxycarbonyl or aryloxycarbonyl with a hydrolase and an effective amount of a nucleophile and a base in a constant pH range to form the compound of the formula

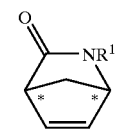

wherein $R^1$ is acyl, alkoxycarbonyl or aryloxycarbonyl, wherein the compound of formula I is then reduced to the compound of formula

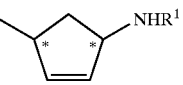

by treatment with a reducing agent, wherein $R^1$ is acyl, alkoxycarbonyl or aryloxycarbonyl, and wherein the compound of the formula IV is then hydrolyzed to the compound of formula V.

13. The method of claim 12, wherein the (1R, 4S)-1-amino-4-(hydroxymethyl)-2-cyclopentene of formula V is isolated after formation.

14. The method of claim 12, wherein the reducing agent is a metal hydride.

15. A method for forming optically active compounds of the formulae

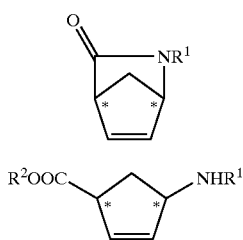

I

II wherein $R^1$ is $C_{1-4}$ alkanoyl which is substituted with one or more halogen atoms, benzylcarbonyl, phenylcarbonyl, methoxycarbonyl, ethoxycarbonyl, propoxycarbonyl, butoxycarbonyl or phenyloxycarbonyl and $R^2$ is a hydrogen atom, the method comprising treating a racemic lactam of the formula

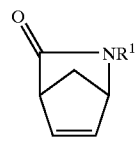

III with a hydrolase and an effective amount of water as nucleophile and a base in a constant pH range to form the optically active compounds of the formulae I and II.

16. The method according to claim 15, wherein a protease or lipase is used as the hydrolase.

17. The method according to claim 16, wherein a serine protease is used as the protease.

18. The method according to claim 17, wherein a subtilisin is used as the serine protease.

19. The method according to claim 15, wherein 2-ethoxycarbonyl-2-azabicyclo[2.2.1]hept-5-ene-3-one is used as the racemic lactam of formula III.

20. The method according to claim 15, wherein treatment of the racemic lactam is conducted in water, a buffer solution or in a mixture of these with an aprotic solvent.

21. The method according to claim 15, wherein the treatment of the racemic lactam is conducted at a temperature of 10 to 60° C.

22. The method according to claim 15, wherein each of the optically active compounds of formulae I and II isolated after formation.

* * * * *